(12) United States Patent
Jung et al.

(10) Patent No.: US 9,091,636 B2
(45) Date of Patent: Jul. 28, 2015

(54) ULTRASONIC PROBE USING REAR-SIDE ACOUSTIC MATCHING LAYER

(75) Inventors: Ho Jung, Seoul (KR); Sung Min Rhim, Incheon-si (KR)

(73) Assignee: HUMANSCAN CO., LTD., Ansan-Si, Gyeonggi-Do (KR)

( * ) Notice: Subject to any disclaimer, the term of this patent is extended or adjusted under 35 U.S.C. 154(b) by 451 days.

(21) Appl. No.: 13/577,301

(22) PCT Filed: Jan. 24, 2011

(86) PCT No.: PCT/KR2011/000462
§ 371 (c)(1),
(2), (4) Date: Aug. 6, 2012

(87) PCT Pub. No.: WO2011/115365
PCT Pub. Date: Sep. 22, 2011

(65) Prior Publication Data
US 2012/0313486 A1 Dec. 13, 2012

(30) Foreign Application Priority Data

Mar. 15, 2010 (KR) .................. 10-2010-0022935

(51) Int. Cl.
*H01L 41/08* (2006.01)
*G01N 29/24* (2006.01)
*A61B 8/00* (2006.01)

(52) U.S. Cl.
CPC ........... *G01N 29/2456* (2013.01); *A61B 8/4483* (2013.01)

(58) Field of Classification Search
CPC ...... H04R 17/00; H03H 9/09; B06B 11/0681; B06B 11/0603; B06B 11/0622; B06B 11/0685; F16F 15/005; G01N 29/2437; G10K 9/122; G10K 11/23; G10K 11/002; G10K 11/02; G10K 11/165

USPC .......................... 310/322, 326, 327, 334, 335
See application file for complete search history.

(56) References Cited

U.S. PATENT DOCUMENTS 4,771,205 A * 9/1988 Mequio .................. 310/334
5,706,564 A * 1/1998 Rhyne .................... 29/25.35
(Continued)

FOREIGN PATENT DOCUMENTS

| JP | 59166139 | 3/1983 |
| JP | 2-264643 | 10/1990 |

(Continued)

OTHER PUBLICATIONS

International Search Report mailed Oct. 13, 2011 for PCT/KR2011/00046.

(Continued)

*Primary Examiner* — Thomas Dougherty
(74) *Attorney, Agent, or Firm* — Lowe Hauptman & Ham LLP

(57) ABSTRACT

The present invention relates to an ultrasonic probe and provides the ultrasonic probe in which acoustic matching layers are formed on both sides of a piezoelectric ceramic capable of simultaneously increasing the signal strength of ultrasonic waves and improving the waveform characteristics of the ultrasonic waves. According to the present invention, a rear-side acoustic matching layer is formed in the upper part of a rear-side block. The piezoelectric ceramic is formed in the upper part of the rear-side acoustic matching layer. A front-side acoustic matching layer is formed in the upper part of the piezoelectric ceramic. Further, an acoustic lens is formed in the upper part of the front-side acoustic matching layer. Particularly, the rear-side acoustic matching layer reflects, toward the acoustic lens, the ultrasonic waves which are propagated to the rear-side block.

6 Claims, 3 Drawing Sheets

(56) References Cited

U.S. PATENT DOCUMENTS

| | | | |
|---|---|---|---|
| 7,678,054 B2* | 3/2010 | Okazaki et al. | 600/459 |
| 8,330,333 B2* | 12/2012 | Harhen et al. | 310/334 |
| 2002/0027400 A1* | 3/2002 | Toda | 310/334 |
| 2005/0122004 A1* | 6/2005 | Shibamoto et al. | 310/334 |
| 2009/0219108 A1* | 9/2009 | Zhao et al. | 333/32 |
| 2010/0198077 A1* | 8/2010 | Ooura et al. | 600/459 |

FOREIGN PATENT DOCUMENTS

| | | |
|---|---|---|
| JP | 03254739 | 11/1991 |
| JP | 7-79815 | 8/1995 |
| JP | 2001-137238 | 5/2001 |
| JP | 2005-198261 | 7/2005 |
| JP | 2007013944 | 1/2007 |
| JP | 2009199302 A | 8/2009 |
| KR | 10-0915485 | 9/2009 |

OTHER PUBLICATIONS

Korean Notice of Allowance for application No. 10-2010-0022935 dated Jun. 26, 2012.

Japanese Office Action for application No. 2012-552791, dated May 7, 2014.

* cited by examiner

ULTRASONIC PROBE USING REAR-SIDE ACOUSTIC MATCHING LAYER

CROSS REFERENCE TO RELATED APPLICATION

This application claims the priority of Korean Patent Application No. 10-2010-0022935, filed on Mar. 15, 2010 in the KIPO (Korean Intellectual Property Office). Further, this application is the National Phase application of International Application No. PCT/KR2011/000462 filed Jan. 24, 2011, which designates the United States and was filed in Korean.

TECHNICAL FIELD

The present invention relates generally to an ultrasonic probe and, more particularly, to an ultrasonic probe which is connected to an ultrasound scan device and transmits/receives ultrasonic waves with improved signal strength and waveform characteristics.

BACKGROUND ART

Ultrasonic waves are used for inspecting the inner parts of the human body or animal or for measuring in a non-destructive manner the thickness or inside combinations of solid matter such as metal or plastic. In these cases, ultrasonic waves are realized in the form of probe (hereinafter, referred to as 'ultrasonic probe') for easy handling by users.

This ultrasonic probe has a structure in which a piezoelectric ceramic is formed on a rear block, a multi-layered acoustic matching layer is formed on the piezoelectric layer, and an acoustic lens is formed on the acoustic matching layer. Therefore, among ultrasonic waves generated from the piezoelectric ceramic, ultrasonic waves propagated toward the rear block are absorbed into the rear block, and ultrasonic waves propagated toward the acoustic matching layer are delivered to an inspection target through the acoustic matching layer and the acoustic lens.

Since in such a conventional ultrasonic probe the ultrasonic waves propagated toward the rear block are absorbed into the rear block, there is a limit to an increase in signal strength of ultrasonic waves propagated through the acoustic lens. Additionally, the ultrasonic waves propagated through the acoustic lens have a narrow bandwidth, which invites poor waveform characteristics.

DETAILED DESCRIPTION OF THE INVENTION

Technical Problems

Accordingly, an object of the present invention is to provide an ultrasonic probe in which an acoustic matching layer is formed on both sides of a piezoelectric ceramic and which not only increases the signal strength of ultrasonic waves but also improves the waveform characteristics of ultrasonic waves.

Technical Solutions

In order to accomplish the above objects, the present invention provides an ultrasonic probe that comprises a rear block, a rear acoustic matching layer, a piezoelectric ceramic, a front acoustic matching layer, and an acoustic lens. The rear acoustic matching layer is formed on an upper side of the rear block. The piezoelectric ceramic is formed on an upper side of the rear acoustic matching layer. The front acoustic matching layer is formed on an upper side of the piezoelectric ceramic. The acoustic lens is formed on an upper side of the front acoustic matching layer.

In the ultrasonic probe of the present invention, each of the rear acoustic matching layer and the front acoustic matching layer may be formed of at least one layer.

In the ultrasonic probe of the present invention, the rear acoustic matching layer may include a first rear acoustic matching layer formed on a lower side of the piezoelectric ceramic, and a second rear acoustic matching layer formed between the first rear acoustic matching layer and the rear block.

In the ultrasonic probe of the present invention, the front acoustic matching layer may include a first front acoustic matching layer formed on an upper side of the piezoelectric ceramic, and a second front acoustic matching layer formed between the first front acoustic matching layer and the acoustic lens.

The ultrasonic probe of the present invention may further comprise a flexible printed circuit board formed between the rear acoustic matching layer and the piezoelectric ceramic and connected to the piezoelectric ceramic.

The ultrasonic probe of the present invention may further comprise a ground plate formed between the front acoustic matching layer and the piezoelectric ceramic and joined to ground patterns of the flexible printed circuit board.

Advantageous Effects

Since having a structure in which the acoustic matching layer is formed on both sides of the piezoelectric ceramic, the ultrasonic probe according to the present invention can increase the signal strength of ultrasonic waves and also improve the waveform characteristics of ultrasonic waves through an acoustic matching of ultrasonic waves which are reflected by the acoustic matching layer formed on the rear side of the piezoelectric ceramic and then are propagated forward.

BEST MODE FOR CARRYING OUT THE INVENTION

Embodiments of the present invention will now be described more fully with reference to the accompanying drawings.

Figure 1:
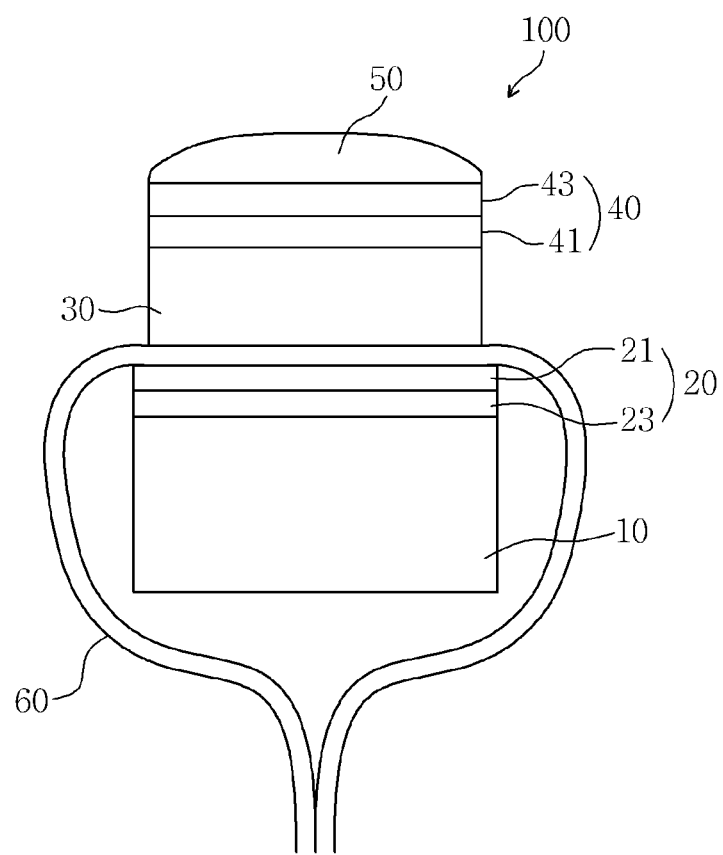
FIG. 1 is a cross-sectional view illustrating an ultrasonic probe in accordance with an embodiment of the present invention.
Figure 2:
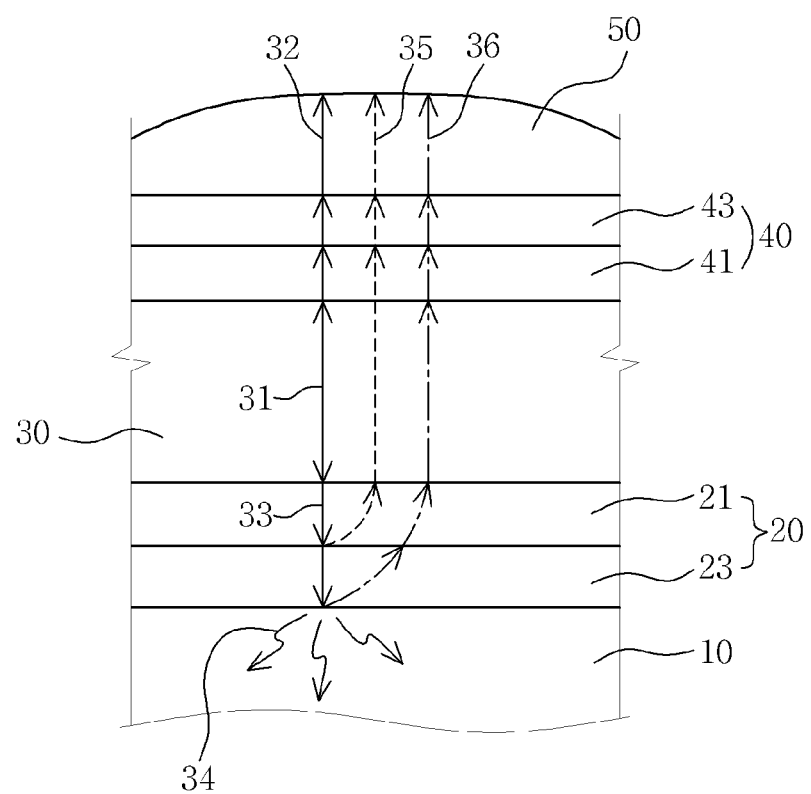
FIG. 2 is an example view illustrating flows of ultrasonic waves generated from a piezoelectric ceramic shown in FIG. 1.

FIG. 1 is a cross-sectional view that illustrates an ultrasonic probe 100 according to an embodiment of the present invention. FIG. 2 shows an example of flows of ultrasonic waves generated from a piezoelectric ceramic 30 shown in FIG. 1. Meanwhile, in order to depict a propagation direction of ultrasonic waves 31 generated from the piezoelectric ceramic 30, a flexible printed circuit board 60 is omitted from FIG. 2.

Referring to FIGS. 1 and 2, the ultrasonic probe 100 according to an embodiment of the present invention includes a rear block 10, a rear acoustic matching layer 20, a piezoelectric ceramic 30, a front acoustic matching layer 40, and an acoustic lens 50, and may further include a flexible printed circuit board 60. The rear acoustic matching layer 20 is formed on an upper side of the rear block 10. The piezoelectric ceramic 30 is formed on an upper side of the rear acoustic matching layer 20. The front acoustic matching layer 40 is formed on an upper side of the piezoelectric ceramic 30. And the acoustic lens 50 is formed on an upper side of the front acoustic matching layer 40. Further, the flexible printed circuit board 60 is formed between the rear acoustic matching layer 20 and the piezoelectric ceramic 30 and electrically connected to the piezoelectric ceramic 30.

Like this, the ultrasonic probe 100 has a structure in which the acoustic matching layers 20 and 40 are formed on both sides of the piezoelectric ceramic 30. Among ultrasonic waves 31 generated from the piezoelectric ceramic 30, the first ultrasonic waves 32 propagated forward (i.e., upward) are matched with the third and fourth ultrasonic waves 35 and 36 which are resulted from the second ultrasonic waves 33 which are propagated backward (i.e., downward), reflected by the rear acoustic matching layer 20, and then propagated forward. Therefore, the ultrasonic waves propagated through the acoustic lens 50 are increased in signal strength and also improved in waveform characteristics.

Now, the ultrasonic probe 100 according to this embodiment will be described in more detail.

The rear block 10 is formed on a lower side of the rear acoustic matching layer 20, and absorbs ultrasonic waves 34 passing through the rear acoustic matching layer 20 among ultrasonic waves 31 generated from the piezoelectric ceramic 30 on the rear acoustic matching layer 20. Rubber, graphite or any other material having excellent sound-absorbing characteristics may be used for the rear block 10.

The rear acoustic matching layer 20 is formed between the piezoelectric ceramic 30 and the rear block 10, and acoustically matches the second ultrasonic waves 33 propagated backward from the piezoelectric ceramic 30 with the first ultrasonic waves 31 propagated forward from the piezoelectric ceramic 30. The rear acoustic matching layer 20 may be formed of at least one layer, e.g., two layers as in this embodiment. Namely, the rear acoustic matching layer 20 includes the first rear acoustic matching layer 21 formed on a lower side of the piezoelectric ceramic 30, and the second rear acoustic matching layer 23 formed between the first rear acoustic matching layer 21 and the rear block 10. For an acoustic matching with the first ultrasonic waves 32 propagated forward from the piezoelectric ceramic 30, the first rear acoustic matching layer 21 changes the acoustic impedance of the third ultrasonic waves 35 reflected from the second ultrasonic waves 33 propagated backward from the piezoelectric ceramic 30 and, ultimately, improves the waveform characteristics of ultrasonic waves passing through and outputted from the acoustic lens 50. Additionally, for an acoustic matching with the first ultrasonic waves 32 propagated forward from the piezoelectric ceramic 30, the second rear acoustic matching layer 23 changes the acoustic impedance of the fourth ultrasonic waves 36 passing through the first rear acoustic matching layer 21 and, ultimately, increases the signal strength of ultrasonic waves passing through and outputted from the acoustic lens 50. The rear acoustic matching layer 20 may be fabricated with metal powder, ceramic powder, silicon wafer, and the like.

The piezoelectric ceramic 30 generates ultrasonic waves 31 by means of piezoelectric effect and is divided into a plurality of devices in a scan direction. The piezoelectric ceramic 30 has electrodes formed on upper and lower sides. Any ceramic material such as PZT and single crystal material such as PMN_PT may be used for the piezoelectric ceramic 30.

The front acoustic matching layer 40 is formed between the piezoelectric ceramic 30 and the acoustic lens 50 and performs an acoustic matching for the first ultrasonic waves 32 propagated forward from the piezoelectric ceramic 30. Also, the front acoustic matching layer 40 performs an acoustic matching for the first, third and fourth ultrasonic waves 32, 35 and 36. Namely, the front acoustic matching layer 40 acoustically matches the piezoelectric ceramic 30 and the acoustic lens 50. The front acoustic matching layer 40 may be formed of at least one layer, e.g., two layers as in this embodiment. The front acoustic matching layer 40 includes the first front acoustic matching layer 41 formed on an upper side of the piezoelectric ceramic 30, and the second front acoustic matching layer 43 formed between the first front acoustic matching layer 41 and the acoustic lens 50. The front acoustic matching layer 40 performs an acoustic matching by gradually changing the acoustic impedance of the first, third and fourth ultrasonic waves 32, 35 and 36 from the piezoelectric ceramic 30 to the acoustic lens 50. Meanwhile, the front acoustic matching layer 40 may be fabricated with metal powder, ceramic powder, silicon wafer, and the like.

The acoustic lens 50 is formed on an upper side of the front acoustic matching layer 40. The acoustic lens 50 concentrates transmitting ultrasonic waves 32, 35 and 36 in order to enhance resolving power of ultrasonic images and then provides them to an inspection target. For example, silicone similar to a living body or any other equivalent may be used for the acoustic lens 50.

The flexible printed circuit board 60 is formed between the rear acoustic matching layer 20 and the piezoelectric ceramic 30 and electrically connected to the piezoelectric ceramic 30. Namely, wiring patterns formed on the flexible printed circuit board 60 are electrically connected to electrodes, e.g., signal electrodes and ground electrodes, formed on the lower side of the piezoelectric ceramic 30. As the flexible printed circuit board 60 electrically connected to electrodes of the piezoelectric ceramic 30, a tape wiring board formed of polyimide and having wiring patterns on an upper side thereof may be used. Alternatively, if necessary, any other tape wiring board having wiring patterns on both sides thereof may be used as the flexible printed circuit board 60.

As discussed above, the ultrasonic probe 100 of this embodiment allows ultrasonic waves, which have been typically absorbed into the rear block, to be reflected toward the acoustic lens 50 by using the rear acoustic matching layer 20. This may increase the signal strength of ultrasonic waves and also improve the waveform characteristics of ultrasonic waves.

Figure 3:
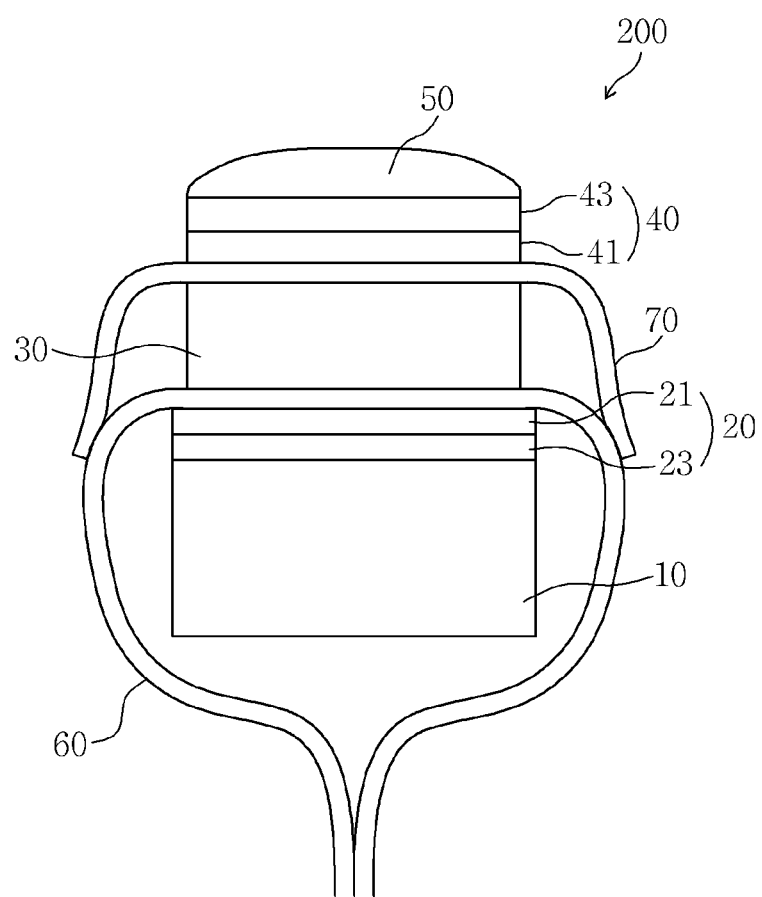
FIG. 3 is a cross-sectional view illustrating an ultrasonic probe in accordance with another embodiment of the present invention.

Meanwhile, in order to enhance the acoustic characteristics of the ultrasonic probe, a ground plate 70 may be further included as shown in FIG. 3. FIG. 3 is a cross-sectional view illustrating an ultrasonic probe 200 in accordance with another embodiment of the present invention.

Referring to FIG. 3, except further having the ground plate 70, the ultrasonic probe 200 according to this embodiment has the same configuration in comparison with the ultrasonic probe 100 shown in FIG. 1. Following descriptions will be focused on the ground plate 70.

The ground plate 70 is formed between the front acoustic matching layer 40 and the piezoelectric ceramic 30. Both ends of the ground plate 70 are joined to wiring patterns of the flexible printed circuit board 60. The ground plate 70, of course, is joined to ground patterns among wiring patterns of the flexible printed circuit board. The ground plate 70 is stacked on an upper side of the piezoelectric ceramic 30, encloses lateral sides of the piezoelectric ceramic 30, and is joined, at both ends thereof, ground patters of the flexible printed circuit board 60. As the ground plate 70, a metal thin film or a ground film having a metal thin film on a lower side thereof, facing an upper side of the piezoelectric ceramic 30 and an upper side of the flexible printed circuit board 60, may be used.

While this invention has been particularly shown and described with reference to an exemplary embodiment thereof, it will be understood by those skilled in the art that various changes in form and details may be made therein without departing from the spirit and scope of the invention as defined by the appended claims.

What is claimed is:

1. An ultrasonic probe comprising:
   a rear block;
   a rear acoustic matching layer formed on an upper side of the rear block;
   a front acoustic matching layer formed on an upper side of the rear acoustic matching layer;
   a piezoelectric ceramic formed between the rear and front acoustic matching layers to generate first ultrasonic waves propagated toward the front acoustic matching layer and second ultrasonic waves propagated toward the rear acoustic matching layer; and
   an acoustic lens formed on an upper side of the front acoustic matching layer,
   wherein the first ultrasonic waves are configured to be acoustically matched with third ultrasonic waves which result from the second ultrasonic waves reflected by the rear acoustic matching layer to improve signal strength and waveform characteristics.

2. The ultrasonic probe of claim 1, wherein each of the rear acoustic matching layer and the front acoustic matching layer is formed of at least one layer.

3. The ultrasonic probe of claim 1, wherein the rear acoustic matching layer includes: a first rear acoustic matching layer formed on a lower side of the piezoelectric ceramic; and a second rear acoustic matching layer formed between the first rear acoustic matching layer and the rear block.

4. The ultrasonic probe of claim 1, wherein the front acoustic matching layer includes: a first front acoustic matching layer formed on an upper side of the piezoelectric ceramic; and a second front acoustic matching layer formed between the first front acoustic matching layer and the acoustic lens.

5. The ultrasonic probe of claim 4, further comprising: a flexible printed circuit board formed between the rear acoustic matching layer and the piezoelectric ceramic and connected to the piezoelectric ceramic.

6. The ultrasonic probe of claim 5, further comprising: a ground plate formed between the front acoustic matching layer and the piezoelectric ceramic and joined to ground patterns of the flexible printed circuit board.

* * * * *